United States Patent
Spelbrink et al.

(10) Patent No.: US 10,034,485 B2
(45) Date of Patent: Jul. 31, 2018

(54) LIPASE IN SHORT-CHAIN ESTERIFICATION OF FATTY ACIDS

(71) Applicant: Coöperatie AVEBE U.A., Veendam (NL)

(72) Inventors: Robin Eric Jacobus Spelbrink, Groningen (NL); Marco Luigi Federico Giuseppin, Gieten (NL); Maarten Robert Egmond, Utrecht (NL)

(73) Assignee: COOPERATIE AVEBE U.A., Veendam (NL)

( * ) Notice: Subject to any disclaimer, the term of this patent is extended or adjusted under 35 U.S.C. 154(b) by 65 days.

(21) Appl. No.: 14/411,954

(22) PCT Filed: Jul. 3, 2013

(86) PCT No.: PCT/NL2013/050489
§ 371 (c)(1),
(2) Date: Dec. 30, 2014

(87) PCT Pub. No.: WO2014/007622
PCT Pub. Date: Jan. 9, 2014

(65) Prior Publication Data
US 2015/0140618 A1 May 21, 2015

(30) Foreign Application Priority Data
Jul. 4, 2012 (EP) .................................. 12174894

(51) Int. Cl.
C12P 7/64 (2006.01)
A23C 19/09 (2006.01)
A23C 19/04 (2006.01)
A23C 19/05 (2006.01)
A23C 19/06 (2006.01)

(52) U.S. Cl.
CPC ........ *A23C 19/0921* (2013.01); *A23C 19/043* (2013.01); *A23C 19/05* (2013.01); *A23C 19/063* (2013.01); *C12P 7/649* (2013.01); *C12P 7/6436* (2013.01); *C12Y 301/01003* (2013.01); *Y02E 50/13* (2013.01)

(58) Field of Classification Search
CPC ........ Y02E 50/13; C12P 7/6436; C12P 7/649; A23C 19/043; A23C 19/063; A23C 19/0921; A23C 19/05; Y02P 20/52; C12Y 301/01003
See application file for complete search history.

(56) References Cited

U.S. PATENT DOCUMENTS

| 6,398,707 B1 | 6/2002 | Wu et al. |
| 2013/0055625 A1 | 3/2013 | Toba et al. |

FOREIGN PATENT DOCUMENTS

| JP | 2011148874 | 8/2011 |
| JP | 2011174028 | 9/2011 |
| JP | 2012077131 | 4/2012 |
| WO | 2008069650 A1 | 6/2008 |
| WO | WO2011159998 | 12/2011 |

OTHER PUBLICATIONS

Andrews D.L. et al., "Characterization of the lipid acyl hydrolase activity of the major potato (*Solanum tuberosum*) tuber protein, patatin, by cloning and abundant expression in a baculovirus vector", Biochem. J., 1988, vol. 252, pp. 199-206.*
Pinsirodom et al, "Selectivity of Celite-Immobilized Patatin (Lipid Acyl Hydrolase) from Potato (*Solanum tuberosum* L.) Tubers in Esterification Reactions as Influenced by Water Activity and Glycerol Analogues of Alcohol Acceptors," Journal of Agricultural and Food Chemistry, American Chemical Society, US, vol. 48, No. 2, pp. 155-160, 2000.
Pinsirodom et al, "Fatty Acid and Product Selectivities of Potato Tuber Lipid Acyl Hydrolase in Esterification Reactions with Glycerol in Organic Media," Journal of the American Oil Chemists' Society, vol. 76, No. 10, pp. 1119-1125, 1999.
Pinsirodom et al, "Selectivity of Potato Tuber Lipid Acyl Hydrolase Toward Long-Chain Unsaturated FA in Esterification Reactions with Glycerol Analogues in Organic Media," Journal of the American Oil Chemists' Society, vol. 80, No. 4, pp. 335-340, 2003.
Macrae et al, "Application of Potato Lipid Acyl Hydrolase for the Synthesis of Monoacylglycerols," Journal of the American Oil Chemists' Society, vol. 75, No. 11, pp. 1489-1494, 1998.
Iso et al, "Production of biodiesel fuel from triglycerides and alcohol using immobilized lipase," Journal of Molecular Catalysis B, Enzymatic, vol. 16, No. 1, pp. 53-58, 2001.
Bjurlin et al, "Composition and Activity of Commercial Triacylglycerol Acylhydrolase Preparations," Journal of the American Oil Chemists' Society, vol. 78, No. 2, pp. 153-160, 2001.
Andrews et al., "Characterization of the lipid acyl hydrolase activity of the major potato (*Solanum tuberosum*) tuber protein, patatin, by cloning and abundant expression in a baculovirus vector," Biochem. J., 1998, 252, pp. 199-206.
Macrae et al., "Application of POtato Lipid Acyl Hydrolase for the Synthesis of Monoacylglycerols," JAOCS, vol. 75, No. 11 (1998), pp. 1489-1494.

* cited by examiner

*Primary Examiner* — Satyendra K Singh
(74) *Attorney, Agent, or Firm* — Hoffmann & Baron, LLP

(57) ABSTRACT

Patatin, a lipase obtainable from potatoes, has been found to have advantages in the esterification reaction of fatty acids to yield fatty acid alkyl esters. Methods for application of this lipase activity are described, as well as the use of patatin in various industrial processes.

5 Claims, 3 Drawing Sheets

100000000
LIPASE IN SHORT-CHAIN ESTERIFICATION OF FATTY ACIDS

This application is the U.S. National Phase of, and Applicant claims priority from, International Patent Application Number PCT/NL2013/050489 filed 3 Jul. 2013, which claims priority from EP 12174894.1 filed 4 Jul. 2012, each of which is incorporated herein by reference.

INTRODUCTION

It is well known that lipases are capable of catalysing the formation of esters in organic media. Thus, using lipases, carboxylic acids can be converted to esters in the presence of sufficient free hydroxy-substituted compounds.

The use of lipases is common in the industry. Examples include racemic drug resolution, fat and lipid modification, flavour synthesis and the production of pharma- and nutraceuticals. The vast majority of lipases that are presently in use are obtained using fungal or bacterial fermentation systems, although animal-derived lipases see some use as well. Plant-derived lipases are relatively rare for industrial applications.

Most industrially applicable lipases are obtained from bacterial fermentation mixtures. Subsequently, the lipases have to be isolated using cumbersome downstream processing. This is a difficult and expensive process, which limits their availability. Therefore, such lipases tend to be of low purity on both a total- and protein-basis and also contain high amounts of carbohydrates, salts and possible undesired side-activities. Furthermore, commercial lipase preparations generally contain a broad variety of non-protein material, salts and non-lipase enzymes (Bjurlin et al 2001 JAOCS 78-2 p 153-160).

Usually, esterification reactions requiring fatty acids rely on the use of fermentation sludges containing high amounts of free fatty acids. This leads to highly variable mixtures, where the free fatty acids are present as a component among many impurities. Phospholipids, present in cell membranes, are an important constituent of these impurities. For example, the commonly used lipase enzyme Novozyme 435 requires degummed oils in order to produce esters from the oil; the presence of phospholipids inhibits the esterification reaction. Lipases generally have difficulties to cope with high amounts of impurities, which leads to inefficient synthesis of fatty acid esters.

A plant-derived lipase enzyme can be obtained from potato. Potato proteins can be divided into three categories: (i) the patatin family, highly homologous acidic 43 kDa glycoproteins (40-50 wt. % of the potato proteins), (ii) basic 5-25 kDa protease inhibitors (30-40 wt. % of the potato proteins) and (iii) other proteins mostly high molecular weight proteins (10-20 wt. % of the potato proteins). The patatin family is known to have some lipase activity, and can be obtained via a single-step chromatographic process followed by concentration and drying. A highly convenient process for the isolation of among others patatin with high purity is described in application WO2008/069650.

In practice however, potato proteins, including the potato protein lipase called patatin, have been mainly used as feedstock for animals because of a lack of practical commercial use.

SUMMARY OF THE INVENTION

The invention provides a means of using patatin for the synthesis of specific esters. Thus, patatin can be used to make esters from $C_4$-$C_{26}$ fatty acids, preferably $C_4$-$C_{12}$ fatty acids and more preferably $C_6$-$C_{10}$ fatty acids, most preferably $C_8$-$C_{10}$ fatty acids. Esters obtained with the method of the invention are prepared from $C_1$-$C_3$ alcohols, preferably monohydroxyalcohols, more preferably ethanol or methanol, and most preferably methanol.

DETAILED DESCRIPTION

Figure 1:
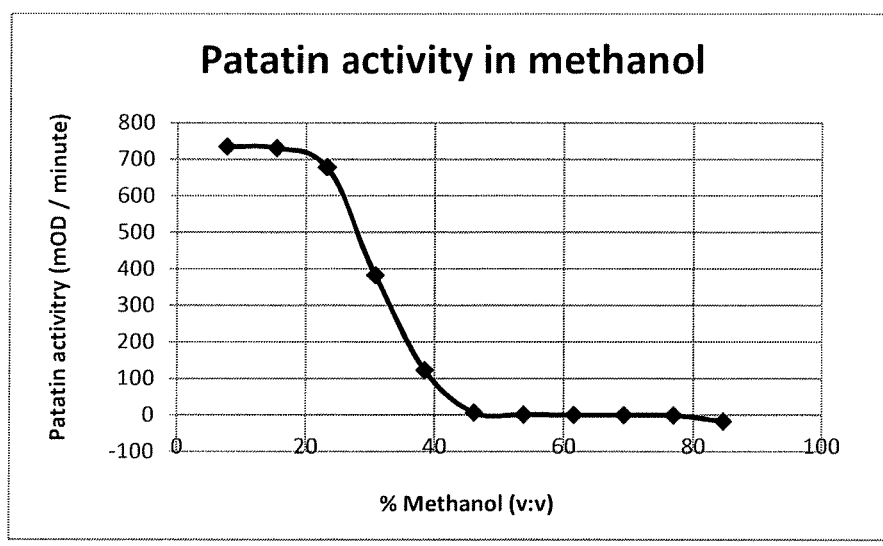
FIG. 1: Residual lipase activity at varying methanol concentrations

For the scope of the present invention, patatin is understood to mean the high molecular weight (HMW) fraction of native potato protein isolates, a highly homologous family of glycoproteins having a molecular weight of 30 kDa or more, preferably 35 kDa or more and more preferably of about 43 kDa, and an isoelectric point of less than 5.8, preferably between 4.8 and 5.5, which makes up about 40-50 wt. % of the potato proteins. Patatin is a family of glycoproteins that displays acyl-hydrolase reactivity and accounts for up to 40 wt % of the total soluble protein in potato tubers. In application WO2008/069650 an elaborate description of the isolation of patatin from potato fruit juice (PFJ) or potato fruit water (PFW) is described, which is incorporated herein by reference.

That process entails subjecting potato fruit juice to a flocculation by a divalent metal cation at a pH of 7-9, and centrifuging the flocculated potato fruit juice, thereby forming a supernatant. Subsequently, the supernatant is subjected to expanded bed adsorption chromatography operated at a pH of less than 11, and a temperature of 5-35° C. using an adsorbent capable of binding potato protein, thereby adsorbing the native potato protein to the adsorbent. Finally, at least one native potato protein isolate is eluted from the adsorbent with an eluent. This method results among others in isolated native patatin of high purity, with a minimum of denatured protein present and characterised by a stable solubility.

The potato fruit juice is pre-treated with a divalent metal cation at a pH of 7-9, preferably 7.0-7.5, to flocculate undesired material, followed by a separation of the flocks by centrifugation. A particularly suitable divalent metal cation is $Ca^{2+}$. This pre-treatment removes undesired material such as negatively charged polymers, pectins, glycoalkaloids, and micro-organisms from the potato fruit juice. In particular, the removal of pectins and glycoalkaloids is advantageous, since these compounds adhere to the potato proteins and may cause flocculation, thereby leading to an unstable protein isolate in terms of solubility and other physical properties.

In the second step of the process, the supernatant is subjected to expanded bed adsorption chromatography. It is advantageous to keep the temperature of the starting material below 35° C. for a better stability of patatin. Furthermore it is preferred to use a moderately high flow rate, typically in the range of 600-1 200 cm/h. The expanded bed adsorption chromatography is operated at a pH of less than 11, preferably at a pH of less than 10.

The native potato proteins in the pre-treated potato fruit juice are isolated from the supernatant by binding them onto a suitable adsorbent in the expanded bed adsorption column. Column materials that bind certain amounts of native potato proteins include mixed-mode adsorbentia such as Amersham Streamline™ Direct CST I (GE Healthcare), Fastline adsorbentia (Upfront Chromatography A/S), macroporous adsorbentia such as Amberlite™ XAD7HP (Röhm & Haas Company) and ion exchange adsorbents. The adsorbent with adsorbed native potato proteins is subsequently eluted with a suitable eluent in order to retrieve the native potato protein isolate, such as patatin. The eluent preferably has a pH in the range of 4-12, more preferably in the range of 5.5-11.0.

In a preferred embodiment using mixed-mode adsorbentia the proteins can be fractionated to both isoelectric point and molecular weight. This allows separation of for instance patatin and protease inhibitor fractions. Patatin isolates are eluted at a pH of 5.7-8.7, preferably at a pH of 5.8-6.5.

Acyl-hydrolase reactivity is generally understood as the ability of a (class of enzyme(s) to catalyse the hydrolysis of an ester bond by a water molecule to form the constituent carboxylic acid and alcohol. This reaction can be reversed by suitable adaptation of the reaction conditions, in which case esterification of a carboxylic acid and an alcohol occurs. Reaction conditions that may influence the direction of the reaction include for instance temperature, reactant identity, and/or the amount of water, carboxylic acid and alcohol present.

In accordance with the present invention it has been found that patatin has a relatively sturdy resistance against an organic environment. In addition, because patatin is isolated from common plant material, it is easy to obtain in large quantities, much easier than the isolated lipases obtained from a fermentation broth and cumbersome downstream processing.

For this reason, patatin is highly suitable for preparation of esters of $C_4$-$C_{26}$ fatty acids, preferably $C_4$-$C_{12}$ fatty acids and more preferably $C_6$-$C_{10}$ fatty acids, most preferably $C_8$-$C_{10}$ fatty acids. The esters are obtained by reaction with alcohols, preferably small molecular alcohols, i.e. $C_1$-$C_3$ alcohols. The small molecular alcohols may be supplied pure or as a mixture of several small molecular alcohols. Preferably, monohydroxyalcohols are used, even more preferably ethanol or methanol, and most preferably methanol.

In a preferred embodiment, methyl and ethyl esters of $C_4$-$C_{26}$ fatty acids, preferably $C_4$-$C_{12}$ fatty acids and more preferably $C_6$-$C_{10}$ fatty acids, most preferably $C_8$-$C_{10}$ fatty acids are prepared, using $C_1$ or $C_2$ monohydroxyalcohols, i.e. methanol or ethanol, or a mixture thereof.

According to the present invention it has been discovered that the acyl hydrolase reactivity of patatin according to the present invention can result in esterification of fatty acids with small molecular alcohols. This way, the acyl-hydrolase reactivity of patatin can be used to synthesize esters. Therefore, patatin can be used in a method for the production of short-chain fatty acid alkyl esters, even if this mixture contains large amounts of impurities.

Thus, the present invention is directed to a method for preparing, preferably selectively, a fatty acid alkyl ester comprising providing a liquid medium comprising one or more $C_4$-$C_{26}$ fatty acids, one or more $C_1$-$C_3$ alcohols and native patatin and allowing the one or more fatty acids to react with the one or more alcohols to obtain the fatty acid alkyl ester.

In a method according to the present invention, the fatty acids are $C_4$-$C_{26}$ fatty acids, preferably $C_4$-$C_{12}$ fatty acids, more preferably $C_6$-$C_{10}$ fatty acids and most preferably $C_8$-$C_{10}$ fatty acids.

The one or more $C_1$-$C_3$ alcohols are comprise preferably one or more monohydroxyalcohols, among which n-propanol, i-propanol, ethanol and/or methanol, and more preferably methanol and/or ethanol are used.

In a much preferred embodiment, the alcohol is methanol and/or ethanol, the fatty acid is a $C_4$-$C_{12}$ fatty acid, and the fatty acid alkyl ester is a methyl or ethyl ester of a $C_4$-$C_{12}$ fatty acid.

Fatty acid chains are categorised by chain length as short to very long:
  Short-chain fatty acids (SCFA) are fatty acids shorter than $C_6$.
  Medium-chain fatty acids (MCFA) are $C_6$-$C_{12}$ fatty acids.
  Long-chain fatty acids (LCFA) are $C_{13}$-$C_{21}$ fatty acids
  Very long chain fatty acids (VLCFA) are fatty acids longer than $C_{22}$.

Generally, lipases are sensitive to impurities present in the esterification mixture. Patatin, on the other hand, is much less sensitive to impurities, in particular to phospholipids. Thus, an advantage of the method of the present invention is that the fatty acid feed stock may contain higher amounts of impurities, in particular phospholipids, than for other lipases.

In other enzyme-based esterification reactions, the presence of phospholipids often inhibits the esterification reaction. For this reason, phospholipids have to be removed from the fatty acid feed stock. This leads to a more expensive feed stock, and thus to a more expensive product. Thus, the ester products can be made much cheaper using patatin than with other lipase-based esterification processes.

The fatty acids in the method of the present invention can be supplied by a fatty acid feed stock. This feed stock is a solid or liquid medium comprising, among others, fatty acids for use in the present invention. Preferably, the feed stock is a liquid medium. The liquid medium may comprise a solvent, but it is also possible to carry out the method of the invention without the use of a solvent, e.g. under conditions where the medium is molten.

The fatty acid feed stock comprises at least one of the $C_4$-$C_{26}$ fatty acids, or any mixture of $C_4$-$C_{26}$ fatty acids, to result in esters of $C_4$-$C_{26}$ fatty acids. In particular, the feed stock for reaction with an alcohol according to the present invention comprises at least one or any mixture of short or medium chain fatty acids, i.e. $C_4$-$C_{12}$ fatty acids. More preferably the feedstock comprises at least one or any mixture of $C_6$-$C_{10}$ fatty acids, most preferably $C_8$-$C_{10}$ fatty acids. This results in esters of $C_4$-$C_{12}$ fatty acids, preferably of $C_6$-$C_{10}$ fatty acids, most preferably of $C_8$-$C_{10}$ fatty acids.

The fatty acids in the fatty acid feed stock may be present in any form, such as bound to glycerol in the form of mono-, di-, and/or triglycerides, but the feed stock may also comprise phospholipids or partially hydrolysed phospholipids. In addition, fatty acids may be present in the feed stock as free fatty acids. Also, a mixture of any or all of these components may be present, as well as other, non-fatty acid bound components. Preferably however, the fatty acids are present in the feed stock, at least in a significant amount, as free fatty acids. A significant amount in this context is 6 g/L, preferably higher 90 g/L.

It is an advantage of the present method that free fatty acids may be present in relatively large amounts. Most preferable, the amount of free fatty acids, expressed as a percentage of the total amount of fatty acids present in the fatty acid feed stock, is at least 25 wt. %, preferably higher than 40 wt. %, based on the weight of the feed stock.

Examples of suitable fatty acid feed stocks are animal fats or oils, vegetable oils, among which hydrolyzed and/or oxidized vegetable oils such as for example used frying oil, spoiled butter fat and low-quality tallow.

In an alternative embodiment, however, the fatty acid feed stock is a fermentation sludge. Because the use of patatin according to the present method increases the tolerance for impurities, a fermentation sludge feed stock is well-suited for esterification of the fatty acids it contains with alcohols. It is a distinct advantage of the present invention that impurities, among which importantly phospholipids, can be present in the reaction medium in large quantities without impeding the esterification reaction.

The alcohols for use in the present invention are at least one $C_1$-$C_3$ alcohol, preferably a monohydroxyalcohol, and more preferably methanol and/or ethanol. Esters of these alcohols with short-chain fatty acids tend to be highly fragrant, while esters with medium- or long chain fatty acids advantageously can function as biodiesel. Preferably, the $C_1$-$C_3$ monohydroxyalcohols are terminal alcohols, i.e. methanol, ethanol and 1-propanol. More preferably however, the alcohol is a $C_1$-$C_2$ alcohol, i.e. methanol or ethanol. Most preferred however is the use of methanol as a fatty acid acceptor. Shorter-chain alcohols are preferred because of their higher reactivity with fatty acids in the presence of patatin.

In a method according to the present invention, patatin can be present immobilized on a carrier, but is preferably used without a carrier. Carriers for the immobilization of lipases are well known in the art. An example is celite. Thus, it may be present in a dissolved or molecularly dispersed form, depending on the nature of the reaction medium. It is preferred that the patatin is freely suspended in the reaction medium.

A disadvantage of lipases is that they generally require large amounts of salts, such as up to 50% potassium salts, to stabilize them in free solution. Salts, however, have an impeding effect on the esterification reaction of fatty acids because it induces crystallization. For this reason in the prior art lipases are typically used in immobilized form on a carrier. Patatin does not require salt stabilization to be used without a carrier, i.e. in freely suspended in the medium, for which reason it is particularly suitable for esterifying fatty acids with low molecular weight alcohols according to the invention.

As already mentioned, the reaction medium in which the method of the invention is performed is preferably liquid, and comprises at least the fatty acid feed stock and or more alcohols of the invention. In addition, the medium may comprise a solvent such as water and/or an organic compound such as a solvent, for example an aliphatic compound, an ether, ester or aromatic compound.

It is an advantage of the use of patatin that a significant amount of water may be present during the esterification reaction. Thus, the invention can function with a water content in the reaction medium of up to 91 vol. %, based on the volume of the reaction medium. Preferably however, the water content is lower than 73 vol. %, even more preferably lower than 40 vol. %, more preferably below 19 vol. %, based on the volume of the reaction medium. In case the water content in the reaction medium is above 50 vol. % based on the volume of the reaction medium, it is called aqueous.

However, the method of the invention may also be performed in an essentially organic medium, at a water content of below 50 vol. %, based on the volume of the reaction medium. In that case, the water content in the reaction vessel may be as low as 5 vol. %, or even be as low as 2 vol. %, based on the volume of the reaction medium. It is preferred that at least some water, i.e. at least 2 vol. %, based on the volume of the reaction medium, is present, even if the method is carried out in an essentially organic medium.

In case the medium is an essentially organic medium, the fatty acid feed stock is diluted with at least the alcohol of the present invention, which may function as a solvent as well as a reactant in this embodiment. It is also possible to use a different solvent, which may be suitably selected to achieve a ready dissolution of all the reaction components. Suitable examples include octane, iso-octane, pentane, hexane, heptane, petroleum ether and butanol. Preferred solvents are octane and iso-octane. It will be understood that it is also possible to use a combination of solvents, including a combination of one or more solvent and the alcohol functioning as solvent.

The concentration of fatty acids in the reaction medium is preferably between 12 and 84 wt. %, based on the weight of the reaction medium. Preferably, these fatty acids are present in the form of free fatty acids.

The concentration of the alcohol in the reaction medium is preferably in slight molar excess relative to the free fatty acids. In molten medium, the free fatty acid is preferably present in concentrations above 80 wt. %, more preferably above 84 wt. %, based on the weight of the reaction medium. In organic solvent, the free fatty acid is present in concentrations above 10 wt. %, more preferably 12 wt. %, based on the weight of the reaction medium.

Generally, the patatin is present in a concentration of 1 wt. %, more preferably 10 wt. %, based on the amount of fatty acid.

Thus, the invention also discloses a method for the preparation, preferably selectively, of a fatty acid alkyl ester comprising mixing in any order native patatin with fatty acids, one or more alcohols and optionally other components, wherein the mixture comprises significant amounts of phospholipids, and allow esterification to occur, wherein the fatty acids preferably comprise short or medium-chain fatty acids, and wherein the alcohols are $C_1$-$C_3$ monohydroxyalcohols, preferably methanol and/or ethanol, and wherein the fatty acid alkyl ester is a $C_1$-$C_3$ ester of a $C_4$-$C_{12}$ fatty acid, preferably a methyl or ethyl ester. If the patatin is used without being immobilized on a carrier, which is preferred, the mixing is preferably carried out such that the patatin will be freely suspended in the reaction medium. In an alternative embodiment the alcohol can advantageously be added in aliquots at distinct intervals or continuously throughout the reaction to control the reaction rate and to avoid enzyme denaturation. Of course, in order to achieve a good yield of the reaction, the total amount of alcohol will have to be sufficient to achieve the desired conversion.

In a preferred embodiment, a method according to the invention is carried out in the absence of an additional solvent. In that case, the reaction medium comprises fatty acid feed stock comprising short or medium-chain fatty acids, and the alcohol, preferably methanol or ethanol. In accordance with this embodiment, the method is preferably carried out under conditions where the medium is molten.

The reaction conditions can be optimized by the skilled person on the basis of his common general knowledge. For instance, the reaction temperature is not critical as long as it does not affect the stability and reactivity of the patatin. Preferably, the reaction is carried out under ambient conditions, or at a temperature above the melting point of the fatty acid feed stock. Suitable reaction temperatures generally lie between 10 and 75° C., preferably between 15 and 60° C., more preferably between 20 and 45° C.

Preferably, the fatty acid alkyl esters that are obtained are isolated from the reaction mixture and optionally further purified, for example by distillation, liquid-liquid extraction or supercritical $CO_2$ extraction.

The method of the present invention can conveniently be used for producing biodiesel. Thus, the present invention discloses a method for producing biodiesel, comprising mixing patatin with a fatty acid feed stock and with one or more $C_1$-$C_3$ alcohols, wherein the fatty acid feed stock comprises one or more $C_4$-$C_{26}$ fatty acids, and allowing the one or more fatty acids to react with the one or more alcohols. In this method, the patatin is preferably freely suspended in the feed stock.

It is especially advantageous to use patatin in this method, because patatin is easily accessible from a common plant, and can be isolated in large quantities. Also, patatin can produce biodiesel from a feedstock comprising relatively large amounts of impurities such as phospholipids. Finally, the presence of salt raises the melting point of fatty acids to be converted to biodiesel. Because in contrast to other lipases, salt stabilization of freely suspended patatin is not required, the negative effect of the presence of salt during biodiesel production is avoided when using patatin. This results in fatty acid alkyl esters according to the present invention, which can be used as biodiesel.

The invention is further illustrated by the following, non-restrictive examples.

Example 1: Lipase Activity in Organic Solvent

Many lipolytic processes are carried out in organic solvents or in aqueous mixtures of such solvents. A prime example is the production of biodiesel from triglycerides or free fatty acids. In these cases, low MW alcohols are used as acyl acceptors to form fatty acid alkyl esters (FAAEs). The alcohols are both reactant and solvent. Methanol is the preferred alcohol because of the price and the quality of the resulting biodiesel.

Such an approach can tolerate water in the reaction mixture, but does require enzymes that survive high concentrations of alcohol to provide the driving force for the reaction to occur.

Patatin (Solanic 206P) was brought into contact with 1 mM of the chromogenic paranitrophenyl butyrate in 10 mM pH 6.5 buffer at varying methanol concentrations. Patatin activities in these systems were determined by measuring the increase in absorbence at 405 nm on a BioRad Model 680 plate reader and are expressed in mOD/minute. The results show that patatin can tolerate up to 20% methanol without loss of activity, and that more than 40% methanol can be present before all activity is lost.

Example 2: Synthesis of Fatty Acid Alkyl Esters by Patatin in Molten Substrate 10 mg of patatin (Solanic 206P) in 100 μL demiwater were brought into contact with 5 mmol (1.0 g) of lauric acid (Merck 8.05333) and an equimolar amount of either methanol (Merck 1.06007), ethanol (Prolabo 83804.360), n-propanol (Alfa Aesar A19902), isopropanol (Prolabo 437423R) or n-butanol (Merck 1.01990). Demineralised water was added to create a 20% (v:v) alcoholic solution in water. The mixtures were incubated overnight at 45° C. under vigorous agitation.

A reference fatty acid methyl ester (FAME) was prepared by dissolving 1 gram of coconut fat (SigmaAldrich C1758) in 100 mL of methanol contain 1.85% of concentrated hydrochloric acid (Merck 1.00317) and refluxing the mixture for 4 hours. The reaction product was evaporated to yield a clear yellow oil.

Reaction products were analysed by TLC on silica plates (Uniplate Z26529-2) that were pretreated with 2.4% boric acid (Fluka 15663) in 50% aqueous ethanol.

Figure 2:
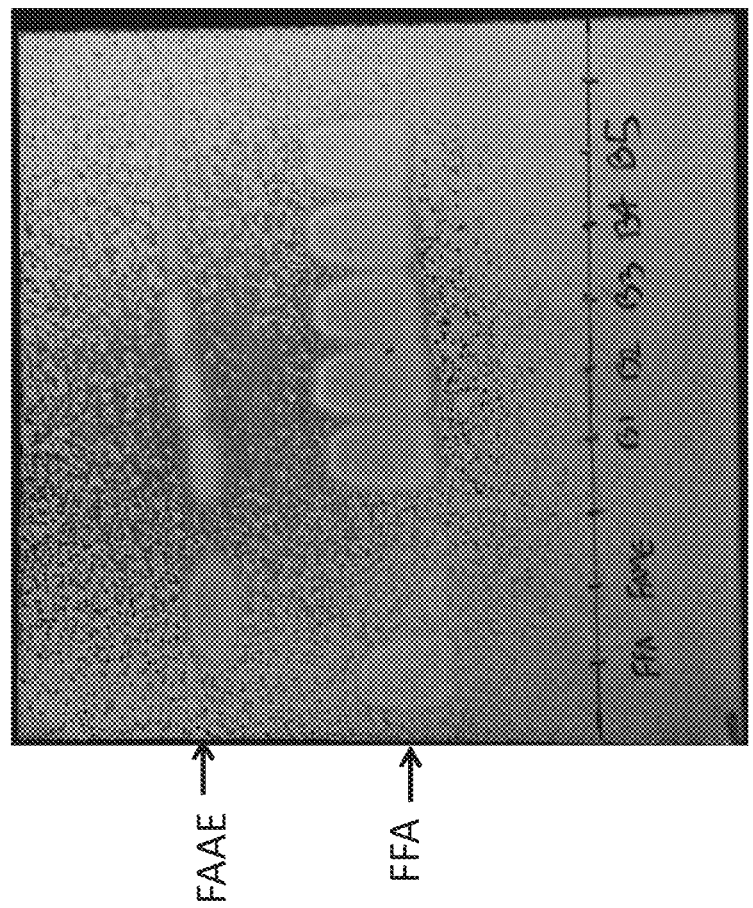
FIG. 2: Thin-layer Chromatogram of Fatty Acid Alkyl Esters (FAAE) synthesised by patatin. Lane 1 contains free fatty acid (FFA, specifically lauric acid, $C_{12}$), lane 2 contains coconut-oil based FAME, lanes 3 through 7 contain the reaction products of lauric acid with methanol, ethanol, n-propanol, isopropanol and n-butanol respectively.
Figure 3:
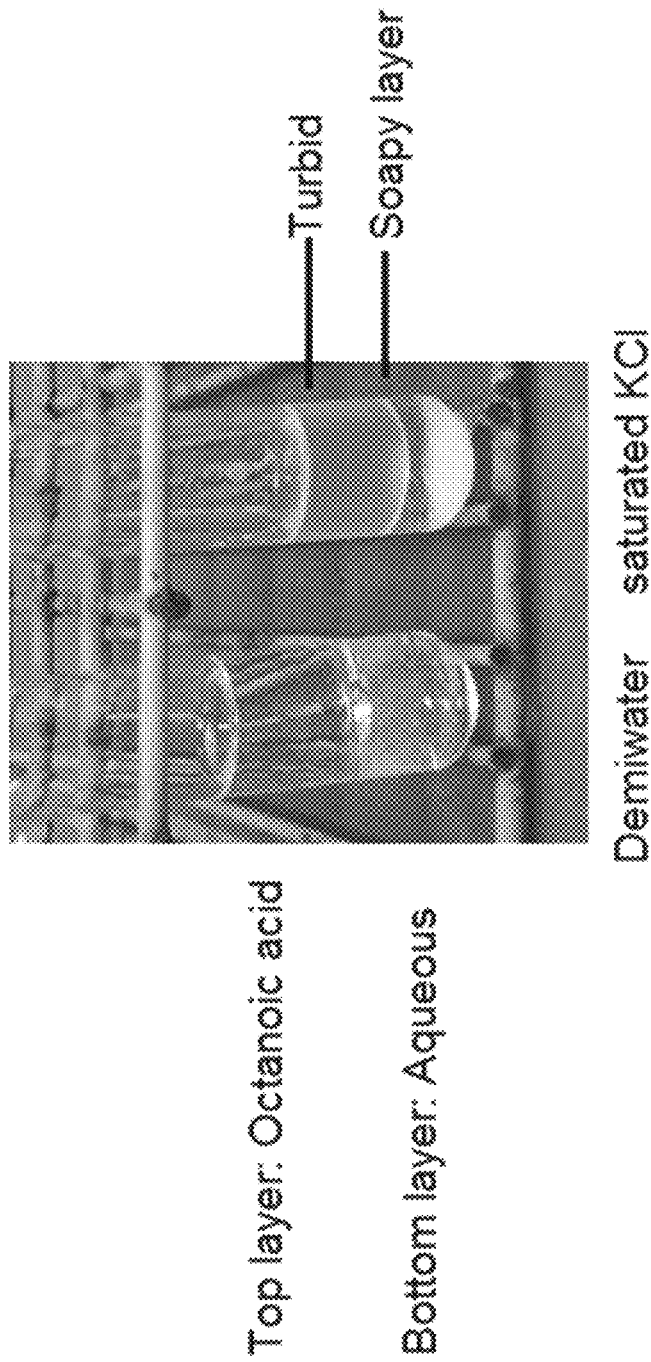
FIG. 3: Precipitation of fatty acids in the presence of increased salt concentration. Left: non-precipitated octanoic acid in a biphasic system of octanoic acid and demi-water. Right: precipitation of the fatty acid octanoic acid in a biphasic system of octanoic acid and a saturated aqueous KCl solution.

All samples were diluted 20 times in TLC eluens consisting of n-hexane (Merck 1.04367), ether (Merck 1.00921) and acetic acid (Prolabo 20104.334) in a ratio of 80:20:2 and a single capillary volume was spotted onto the plate. The plate was run in the eluens and dried in the air. The plate was sprayed with concentrated sulphuric acid (Merck 1.00371). This treatment caused lauric acid and its esters to appear as white spots against a blue background (See FIG. 2).

The developed TLC plate shows free lauric acid in lane 1 at roughly the halfway height and FAMEs running close the front in lane 2.

Lauric acid incubated with patatin and alcohols shows residual amounts of free fatty acid halfway from the bottom and fatty acid alkyl esters at the front, near the top of the plate. Patatin catalyses the formation of FAAEs from free fatty acids and small alcohols, with the highest conversion occurring for methanol, ethanol and n-propanol, in that order.

Example 3: Synthesis of Fatty Acid Alkyl Esters by Patatin in Organic Solvent Octanoic acid (Merck 8.00192.1000) and 20% methanol (Merck liChrosolv 1.06007.1000) were mixed in isooctane (SigmaAldrich 360597) so that octanoic acid and methanol were in approximately equimolar quantities (11.0 mL of octanoic acid and 16.8 mL of 20% methanol in isooctane). 500 mg of patatin (Solanic 206P) and 40 mg of water were added. A blank sample was prepared in the same way but leaving out patatin. The reaction was performed in closed tubes which were heated in a water bath with a closed lid. The solutions were incubated for four hours at 50 C. Aliqots were taken from the reaction vessels and diluted 10 times in pure acetonitril (Merck LiChrosolv 1.00030.25007) and analysed by HPLC. The HPLC was outfitted with a reversed phase silica gel column (C18 sepharose), UV-detector operating at 202 nm (Knauer Smartline UV Detector 2600) and a gradient mixer (Smartline Manager 5000 eluent mixer). An acetonitrile gradient was applied for the HPLC experiments 50% acetonitrile eluens was prepared by mixing with milliQ water and 0.5 μm filtration. The column was preconditioned with eluens. Samples were injected directly in acetonitril and eluted on a 50 to 100% acetonitril gradient over the course of 20 minutes. Quantification of fatty acid methyl ester was performed against a calibration curve prepared from pure methyl octanoate (SigmaAldrich 260673-23G).

The patatin sample showed a 12% conversion of octanoic acid into the corresponding methyl ester, indicating successful esterification.

Example 4: Phospholipase Activity of Patatin

Phospholipids of distinct acyl chain lengths were dispersed in aqueous solutions containing 0.5% gum Arabic and 100 mM of Triton X100 by sonicating for 30 minutes. Patatin was added in quantities up to 100 mg and the consumption of sodium hydroxide was monitored by means of a pH stat setup operating at pH 7.5.

Diacyl-glycerophosphocholines of chain lengths up to 9 are susceptible towards patatin hydrolysis.

TABLE 2

Patatin activity towards various substrates in mmol/minute/g patatin at ambient temperature.

| Chain length | 1,2-diacyl-sn-3-glycerophosphocholine |
|---|---|
| 6 | 0.5 |
| 7 | 5.6 |
| 8 | 20.7 |
| 9 | 40.7 |
| 10 | 0.6 |

This experiment shows that patatin is capable of hydrolysing phospholipids, for which reason it is expected not to be deactivated by the presence of phospholipids in an esterification medium.

Example 5: Effect of Salt on Free Fatty Acids 1 mL aliquots of octanoic acid (Merck 8.00192.1000) were mixed with either demineralised water or a saturated potassium chloride (SigmaAldrich P9311) solution and briefly heated to 50° C. Upon cooling, the octanoic acid-salt solution mixture showed turbidity in the organic phase and a soapy scum on the interface while the octanoic acid-water mixture remained clear and free of soap. Turbidity indicates partial precipitation. The results show that the presence of salt makes the handling of free fatty acids more difficult.

The invention claimed is:

1. A method for selectively preparing a fatty acid alkyl ester comprising:
providing a liquid reaction medium comprising a fatty acid feedstock, said fatty acid feedstock comprising one or more $C_4$-$C_{26}$ fatty acids and at least 6 g/L free fatty acids, said liquid reaction medium further comprising one or more $C_1$-$C_3$ alcohols and an effective amount of native patatin; and
allowing the one or more fatty acids in the liquid reaction medium to react with the native patatin and the one or more $C_1$-$C_3$ alcohols to obtain the fatty acid alkyl ester,
wherein the native patatin is present in said liquid reaction medium in a dissolved or a dispersed form, wherein said liquid reaction medium is an organic medium having a water content below 50% by volume, and wherein the alcohol is at least one $C_1$-$C_3$ monohydroxy-alcohol.

2. The method according to claim 1, wherein said native patatin is freely suspended in the liquid reaction medium.

3. The method according to claim 1, wherein the alcohol is methanol and/or ethanol, wherein the fatty acid is a $C_4$-$C_{12}$ fatty acid, and wherein the fatty acid alkyl ester obtained is a methyl or ethyl ester of the $C_4$-$C_{12}$ fatty acid.

4. The method according to claim 1, wherein the liquid reaction medium comprises only fatty acid feedstock containing $C_4$-$C_{12}$ fatty acids, methanol or ethanol, and the native patatin.

5. The method according to claim 1, wherein the alcohol is methanol.

* * * * *